United States Patent [19]
Wilson

[11] Patent Number: 6,113,550
[45] Date of Patent: Sep. 5, 2000

[54] PLETHYSMOGRAPH

[75] Inventor: Stephen James Wilson, Camp Hill, Australia

[73] Assignee: The University of Queensland, St. Lucia, Australia

[21] Appl. No.: 09/124,926

[22] Filed: Jul. 29, 1998

[30] Foreign Application Priority Data

Jul. 29, 1997 [AU] Australia ................... PO8300

[51] Int. Cl.[7] ................................ A61N 5/00
[52] U.S. Cl. ............................ 600/534; 600/22
[58] Field of Search ................... 600/529–534, 600/22, 21; 128/897–899

[56] References Cited

U.S. PATENT DOCUMENTS

| | | | |
|---|---|---|---|
| 3,658,052 | 4/1972 | Alter | 600/534 |
| 3,831,586 | 8/1974 | Petit | 600/534 |
| 5,241,300 | 8/1993 | Buschmann | 600/534 |

Primary Examiner—Cary O'Connor
Assistant Examiner—Michael Astorino
Attorney, Agent, or Firm—Knobbe, Martens, Olson & Bear, LLP

[57] ABSTRACT

Non invasive measurement of infant lung function during unsedated sleep is achieved by a plethysmograph which comprises of a rigid acrylic box (10) with integral water sealed spirometer (11) and a vacuum-actuated neck seal (20) allowing "head out" monitoring. The neck seal comprises particulate material entrapped in the space between two layers of rubber, which become rigid when a vacuum is applied to the space. Tidal volume, respiratory rate and changes in functional residual capacity (FRC) are able to be recorded during unsedated REM and NREM sleep whilst monitoring with conventional polysomnographic methods. The head out configuration allows additional instrumentation to be used, avoids facial stimulation and allows unimpeded access to the upper airway.

17 Claims, 5 Drawing Sheets

PLETHYSMOGRAPH

THIS INVENTION relates to a volume displacement plethysmograph for investigating pulmonary function, particularly of infants, The invention also relates to a seal suitable for use in the plethysmograph.

BACKGROUND ART

Objective assessment of respiratory function plays an important part in understanding the physiology and pathophysiology of the respiratory system. Lung function is an indispensable tool for diagnosis and monitoring of respiratory disease states in adults and older children, but has not gained wide acceptance in the management of infant lung disease. The primary difficulty in measuring infant lung function is the inherent lack of cooperation requiring assessment during sedated sleep and the use of a face mask. To date there is no widely applied technique for the measuring infant lung function in the unsedated infant.

Some methods of monitoring respiration in an infant have been developed for specific needs. Known devices for monitoring infant lung function can generally be classified as either invasive or non-invasive with respect to the infant's airway.

Invasive monitoring devices include pneumotacchographs which are connected to a sealed face mask, or spirometers similarly connected to a face mask. Traditional methods of volume and flow measurement with a face mask and/or pneumotachograph induce error through the effects of trigeminal stimulation, increased dead space and resistive loading. Face masks are poorly tolerated in unsedated infants and induce arousal especially in light sleep. They are completely impractical in the awake infant.

In addition it is technically difficult to maintain a seal with the infant for protracted periods of time, thereby limiting the ability to acquire data dynamically during unpredictable respiratory events such as apnoeas, sighs and hypopnoeas. These events are typically associated with desaturation and understanding respiratory dynamics that surround such events forms an important part of sleep medicine.

Non-invasive devices typically use bands to detect changes in chest and abdominal wall dimensions to monitor breathing. Such devices are easier to operate technically, and are less disturbing to the subject. However, these devices generally suffer from inaccuracy in measuring or interpreting lung volume changes.

Respiratory inductance plethysmography (RIP) has been used as one such non invasive measure of tidal volume and minute volume in infants but is compromised by complex and time consuming calibration techniques, though a simplified calibration has been recently disclosed. A pneumotachograph and face mask is still required to calibrate RIP to measure volume accurately and therefore can only be used in very young or sedated infants.

A fundamental problem with RIP is the approximation of the infant respiratory system as a two compartment model. In disease states chest wall motion is complex with subcostal and suprasternal recession being typical features. In infants with respiratory distress syndrome, chest wall recession in the inferior aspect of the chest may occur with expansion in the upper portion of the chest, and it is unlikely that a single RIP band can accurately measure thoracic volume changes in such situations. RIP has not been validated as a measure of tidal volume in infants with lung disease, and it is known to be inaccurate in infants under 1.5 kg presumably because of variable chest wall compliance.

Constant volume plethysmography involves the insertion of the infant in a sealed chamber and the application of a face mask to permit the infant to breathe fresh air and to remove expired air. Occlusion of the airway at the mask results in respiratory efforts by the infant for a small number of breaths. This, in turn, compresses and rarefies the gas within the chamber. By measuring the pressure changes, and knowing the volume of the chamber, Boyle's Law permits an estimate of the total gas within the infant's lung at the time of occlusion. However, the procedure is technically difficult, and the procedure is not suitable for protracted periods of time, e.g. during sleep.

Functional residual capacity (FRC) in infants is dynamically elevated above relaxed end expiratory volume using laryngeal and diaphragmatic breaking together with the commencement of inspiration before end expiration. The mechanism of FRC elevation therefore revolves around an interaction between the expiratory time constant and rate. FRC is usually reported as a single measurement and yet because of the way this volume is achieved by the infant it is likely that a range of volumes more accurately describes FRC. This is probably the case in REM sleep which is characterised by highly variable rate and varying degrees of laryngeal adductor activity.

FRC change with different sleep state has been investigated by different researchers with conflicting results. The concept of FRC variability was investigated using a respiratory jacket. This technique has not gained wide acceptance, presumably due to difficulties with calibration and fitting of the jacket. In order to interpret FRC measurements and indeed lung mechanics which are very dependent on lung volume, it is important to understand the natural degree of variability of FRC.

It is an object of this invention to provide an improved plethysmograph for measuring infant lung function non invasively during unsedated sleep without the need for a face mask.

It is yet another embodiment of this invention to provide an improved seal particularly, but not solely, suitable for use with the plethysmograph.

SUMMARY OF THE INVENTION

In one broad form, this invention provides apparatus for monitoring changes in the volume of a portion of a body, comprising a substantially closed chamber adapted to receive the portion in use, so that the portion is located within the chamber but the remainder of the body is outside the chamber, the chamber being dimensionally constant in use;

an opening in the chamber providing fluid communication between the chamber and a constant pressure, variable volume space partially defined by a movable cover member which moves in response to variation in the volume of the variable volume space; and means for detecting movement of the cover member;

whereby changes in the volume of the portion result in corresponding changes to the volume of the space which are able to be monitored by detecting movement of the cover member.

Typically, the apparatus is used as a plethysmograph for monitoring pulmonary function of a patient.

The patient is typically an infant, but may be an older child or an adult, or even a non-human animal, such as a small mammal.

The patient is located in the chamber in sue, but with the head of the patient outside the chamber a neck seal is used to provide an airtight seal around the patient's neck.

Typically, the opening in the chamber is a port extending into the variable volume space, and a water seal is provided between the cover member and the port.

The cover member is an open-bottom bell structure mounted to a rotatable shaft. The detecting means suitably comprises a linear potentiometer mounted to the shaft. The resistance of the potentiometer varies with the angular position of the shaft. Alternatively, other detecting means, e.g. an optical detector, can be used.

In use, variation of the volume of the body portion, e.g. the chest (and/or abdomen) of the patient through breathing, is detected by movement of the cover member. The cover member is made of thin lightweight material, and imposes minimal back pressure. Hence, even small volume changes can be detected.

Another advantage of this plethysmograph is that it is of economical construction.

A particular advantage of the plethysmograph is that the patient's mouth and/or nose are outside the chamber, and hence the patient can breathe freely without a facial mask.

The neck seal is flexible to permit passage of the patient's head, but is stiffened in use to a substantially rigid form. In this manner, the neck seal does not substantially alter the constant volume of the chamber during pulmonary monitoring operations.

The neck seal is not only suitable for the plethysmograph of this invention, but has wider application. According to another aspect of the invention therefore, there is provided a seal, suitable for sealing the entry of a limb or the like into a chamber, comprising a pair of juxtaposed flexible sheets each having an opening therein, the openings being aligned, the sheets being sealed together around the openings and along a closed figure around, and spaced from, the openings, to define a closed space between the sheets;

particulate material in the closed space; and an opening in one of the sheets to permit the closed space to be connected to a vacuum pump or the like, whereby upon evacuation of air from the closed space, the seal adopts a substantially rigid form.

Typically, the flexible sheets are made of elastomeric material, such as latex rubber.

The particulate material may suitably be particles or beads of expanded polystyrene.

The opening is suitably in the form of a spigot for ease of connection to a tube leading to a vacuum pump.

In order that the invention may be more fully understood and put into practice, a preferred embodiment thereof will now be described with reference to the accompanying drawings.

DESCRIPTION OF PREFERRED EMBODIMENT

Figure 1:
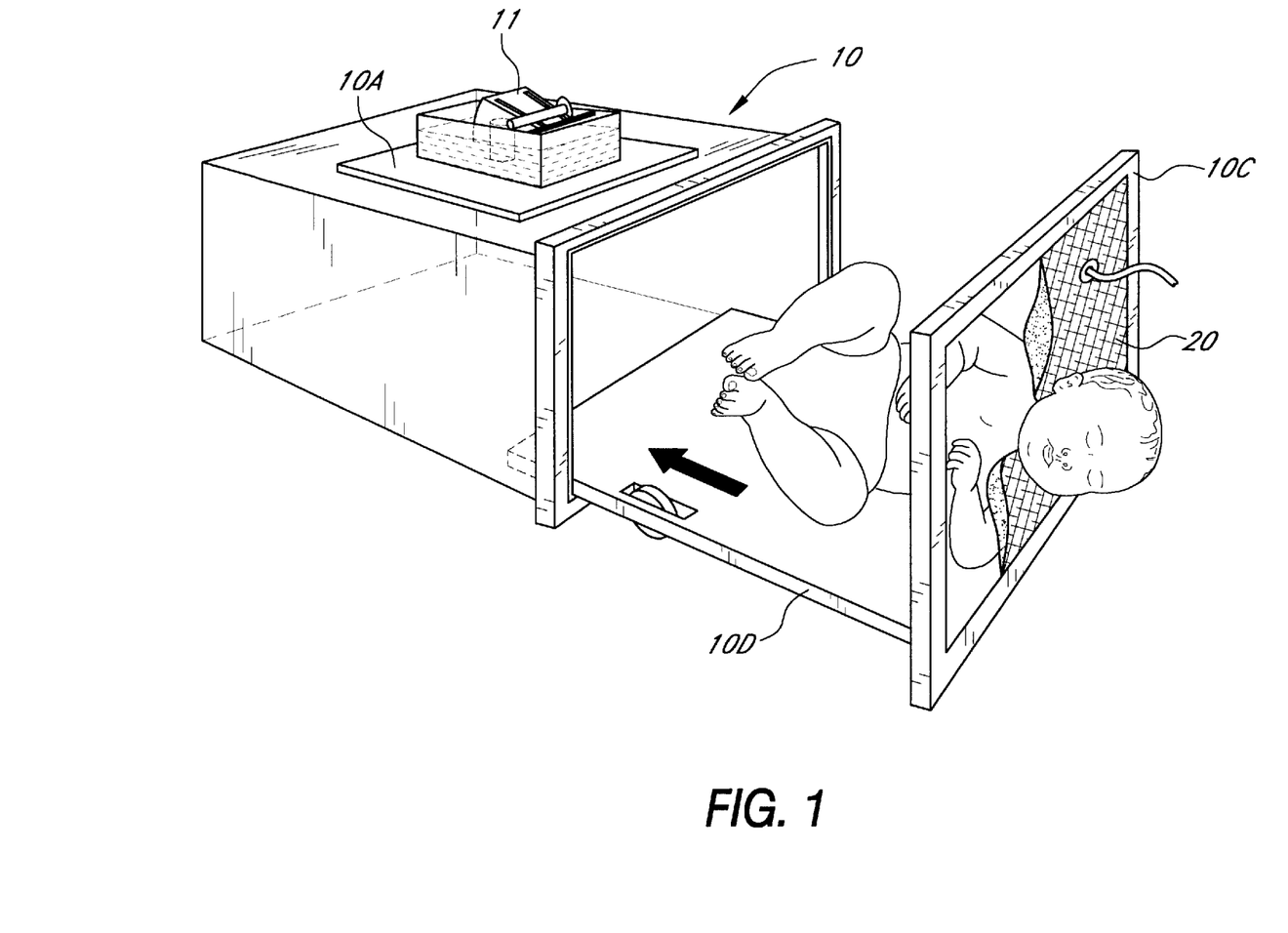
FIG. 1 is a perspective view of a plethysmograph according to one embodiment of the invention with infant.

As shown in FIG. 1, a low body plethysmograph comprises a chamber in the form of a box 10 in which an infant is positioned from the neck down. The sides of the box 10 preferably include transparent portions so that the infant can be visually monitored. In the illustrated embodiment, the box is a rigid clear acrylic box constructed to internal dimensions of 180×320×500 mm to accommodate a range of infants. A removable top plate 10A serves as a base of a water sealed spirometer 11, described in more detail below.

The box 10 is provided with a removable end wall 10C connected to a mattress tray 10D. The mattress tray allows easy access to the infant to aid settling and facilitates insertion of the infant within the device without disturbance.

The end wall 10C is in the form of a rectangular frame having a neck seal 20 therewithin to provide an airtight seal around the neck of the infant. (The neck seal is described in more detail below). A peripheral gasket can be used to provide an airtight seal between the end wall frame 10C and the opposed periphery of the entrance to the box 10.

As can be seen from FIG. 1, the infant's head remains outside of the box 10. This permits the infant to breathe room air easily, as well as the application of therapeutic maneuvers to the infant.

Figure 2:
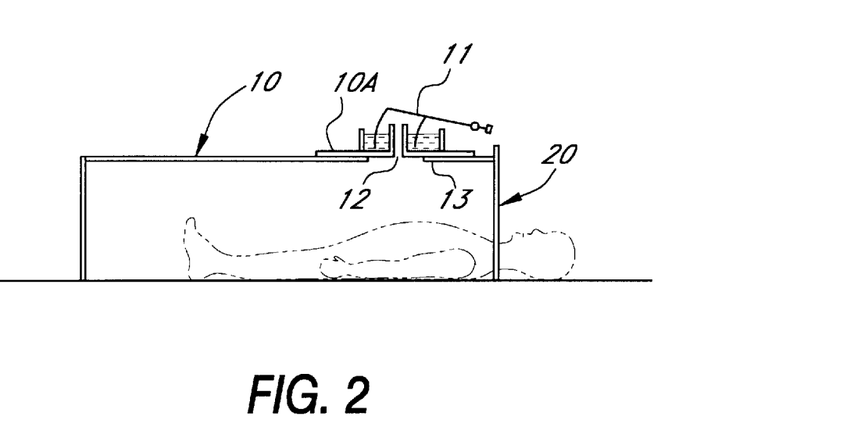
FIG. 2 is a schematic sectional elevation of the plethysmograph of FIG. 1.

Changes in chest and abdominal volumes of the infant during respiration are monitored using a spirometer 11 mounted to the top of the box 10. The spirometer 11 (described in more detail later) is in fluid communication with the interior of the box 10 via a spigot-like port 12 which is preferably located directly over the chest portion of the infant. A water seal 13 is suitably provided around the spirometer 11.

The construction of the plethysmograph is such that it maintains a constant pressure on the infant, as opposed to constant volume chambers used in prior art devices. Although constant pressure chambers had been used previously in adult respiratory medicine, they met with very limited success. The two principal technical problems with known constant pressure chambers were (i) the inability of the spirometer to measure small volume changes, and (ii) the maintenance of an airtight seal around the patient's neck. These problems are overcome by the plethysmograph illustrated in the attached drawings.

Figure 3:
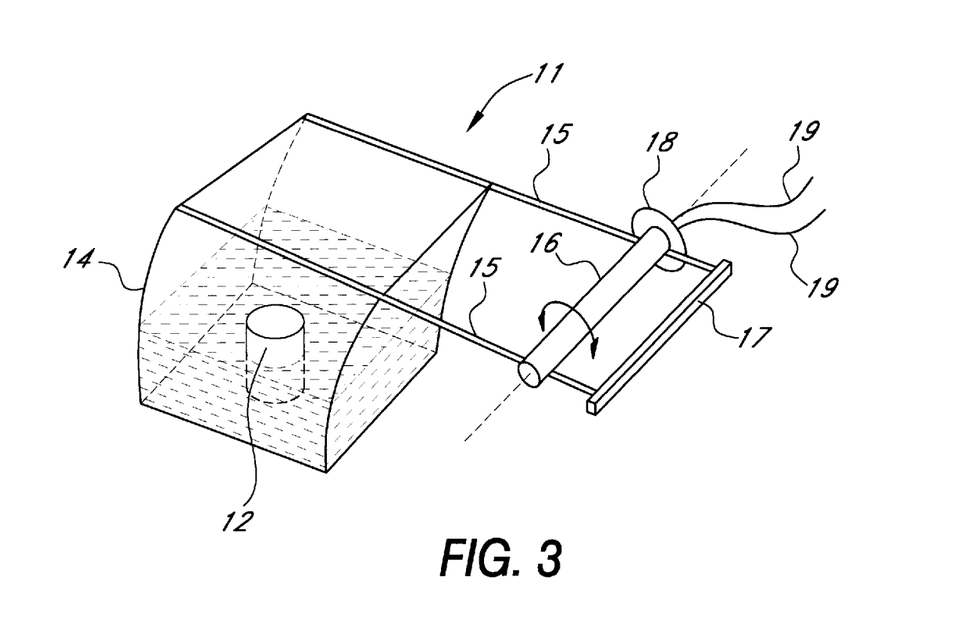
FIG. 3 is a schematic perspective view of a spirometer used in the plethysmograph of FIG. 1.

As shown in FIG. 3, the spirometer 11 used with the plethysmograph comprises an open-bottom cover or "bell" 14 which is connected by radial arms 15 to a rotatably mounted shaft 16. The bell 14 is typically of lightweight polystyrene (volume 120 mL, mass 16 g) and the shaft 16 may be of carbon fibre. A counterweight 17 may also be connected to the rotatable shaft 16, to balance the weight of the bell 14. However, as the bell 14 is lightweight, only a small counterweight (if any) is required.

A linear potentiometer 18 is mounted to the shaft 16. The potentiometer is connected by wires 19 to electronic monitoring apparatus which is able to monitor the rotational position of shaft 16.

The side walls of the bell 14 are immersed in a reservoir of water 13 surrounding the port spigot 12, so that the water forms a seal. Further, two opposed walls of the bell 14 are shaped such that a linear relationship exists between the change of volume within the bell 14 above the water surface and the angle of rotation of the shaft. These walls are of arcuate shape, concentric with the axis of rotation of the shaft 16. This radial pivoting design allows ease of transduction to an electrical signal by the linear potentiometer 18 on the axis of rotation.

The lightweight bell chamber 14 (optionally counterweighted) provides minimal static back pressure (typically less than 1 cm of water). The spirometer 11 is sensitive to very small changes in abdominal and/or chest volume of the infant. Typically, volume changes as small as 2 ml can be detected.

The lightweight spirometer 11 has a single degree of freedom of (radial) movement, thereby minimising phase errors. The illustrated spirometer was employed to measure volume displacements from the box rather than a pneumotachograph because of the superior low frequency response extending to 0 Hz.

Airtight electrical connections can be provided to permit passage of cabling into the box 10 for ECG, oximetry and RIP. A port at the side can also be provided for attachment of a calibrated gas syringe for spirometer calibration.

A circulating fan can be used to provide air mixing within the chamber through a silica gel cartridge and to ensure that recorded box humidity is controlled in the presence of skin losses. Box temperature and humidity can be recorded with battery operated instruments within the chamber. Multichannel signal acquisition and storage is typically performed by a personal computer.

Figure 4:
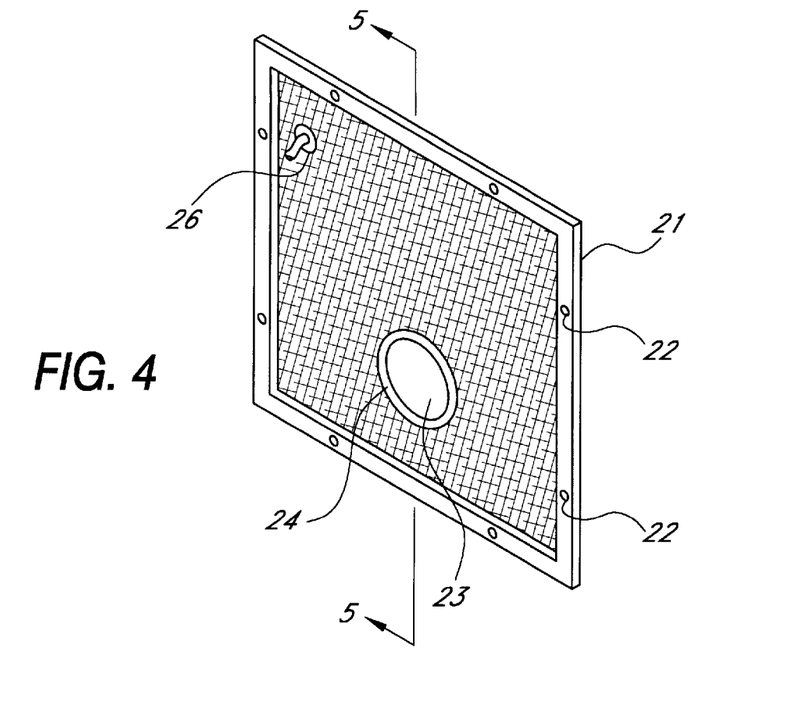
FIG. 4 is a perspective view of a neck seal suitable for use with the plethysmograph of FIG. 1.
Figure 5:
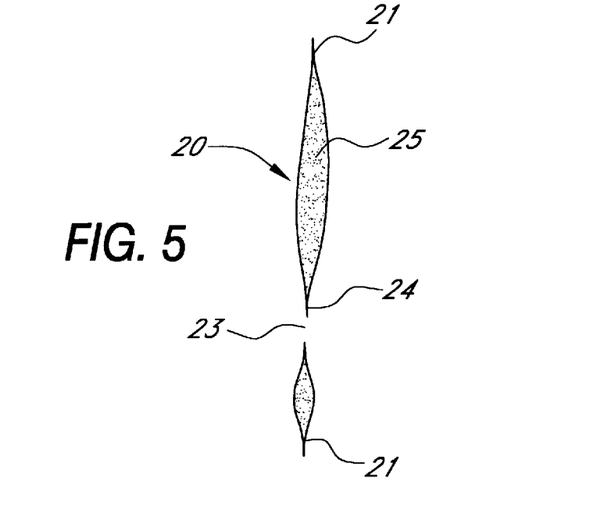
FIG. 5 is a sectional view along A—A of the neck seal of FIG. 4.

The neck seal 20 is shown in more detail in FIGS. 4 and 5. The neck seal satisfies the conflicting requirements of being a compliant membrane to permit its application over the infant's head, yet being rigid in use to maintain dimensional stability of the box 10 and thereby permit any volume change to be faithfully recorded by the spirometer.

The neck seal 20 comprises two layers of elastic material, preferably a natural latex rubber (170 $\mu$m mean thickness). The two layers are sealed together around the periphery 21 of the neck seal. Holes 22 are suitably placed in the sealed periphery 21 to locate the neck seal with the frame 10C and/or the open end of the box 10.

A neck opening 23 is provided in both layers of the neck seal, and the two layers are sealed together at the annular portion 24 around the neck opening. Several neck seals with holes of varying sizes from 30 mm to 55 mm diameter may be provided to accommodate a range of infant neck circumferences.

Particulate material, such as small beads or particles of expanded polystyrene 25, are inserted between the two sealed layers of the neck seal. The particulate material may also be fibrous, stick-like or any other suitable particle components. A spigot 26 is provided on the outer side of the neck seal for connection to a vacuum pump or the like.

In use, with no vacuum applied, the rubber neck seal is stretched over the infant's head and placed around the infant's neck. At this stage, the neck seal is still flexible. The spigot 26 is then connected to the vacuum pump. When the air between the two layers of the neck seal is evacuated to a pressure of −10 to −20 kPa, the two layers of the neck seal compact the particulate materials therebetween and with each other, and form a substantially rigid wall. (That is, the neck seal wall remains rigid for the volume/pressure changes encountered in use).

The frequency response and phase characteristics of the plethysmograph were tested using a loudspeaker driven by sinusoidal signals of variable frequency through a DC coupled amplifier. Box acoustic capacitance was tested by the rapid and slow injection of 100 ml of air while the sealed box pressure was recorded. Spirometer inertance was calculated by the introduction of a varying signal at the spirometer port 12 whilst the pressure was recorded at the point of introduction.

The spirometer 11 was calibrated by inserting known volumes of air into the plethysmograph box 10 using a calibrated gas syringe prior to insertion of the infant. After monitoring devices were applied to the infant a normal feed was given and the settled infant placed on the tray. Moot infants were studied supine but decubitus position and prone position were used successfully. The infant's head was delivered through the neck seal aperture which was stretched open by the operator.

Application of the vacuum then stabilises the seal in an airtight position whilst conforming to the infants sleep position. Any leak at the seal is apparent from a monophasic baseline drift on the spirometer output and data are discharged until the seal is re-established. (This may involve minor positioning maneuvers of the infant's head and neck).

The box temperature elevated 1.5 to 2 degrees Celsius above ambient to a steady state with changes being less than 1.0 degree per hour. Gross body movement which induced artefacts upon the volume signal were edited accordingly.

The capacitance, resistance and inertance of the described plethysmograph and spirometer are shown below (measured with 21 normal saline simulating infant volume).
Acoustic Capacitance: 0.181. kPa$^{-1}$ (0.018 1. cm H$_2$O$^{-1}$)
Resistance: 0.021 kPa.1$^{-1}$ .s(0.21 cm H$_2$O 1$^{-1}$.s$^{-1}$)
Inertance 0.0015 kpa 1$^{-1}$ .s$^2$ (0.015 cm H$_2$O 1$^{-1}$ .s$^2$)

Eight normal infants and seven infants with varying degrees of airway and interstitial lung disease aged from term to three months were successfully studied. Some infants were studied for over two hours, the limiting variable usually being the timing of the next feed. No complications were encountered and most infants settled spontaneously. Difficulties were experienced with some larger infants who were disturbed by the restrictive space within the plethysmograph. One infant failed to settle in the box due to the restrictive space and the study was abandoned. All infants were fed, prepared and settled in the box within one hour.

Figure 6A:
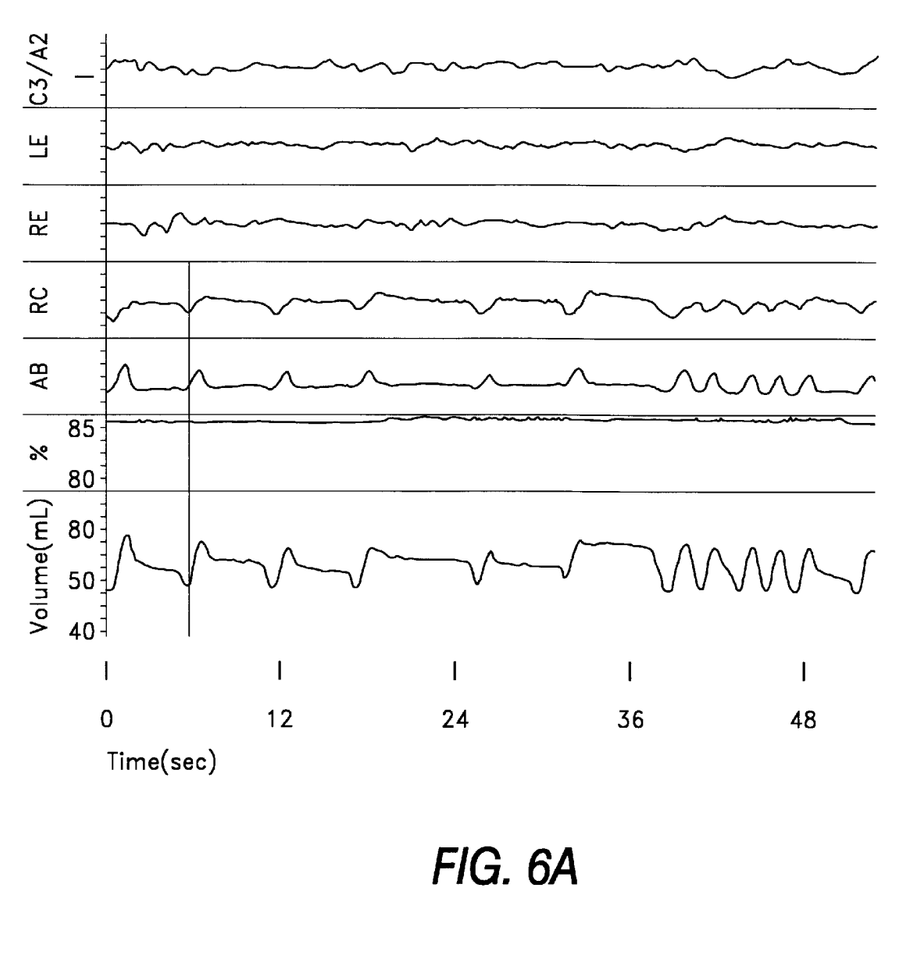
FIGS. 6(a) and 6(b) are polysomnographic recordings from two different infants.
Figure 6B:
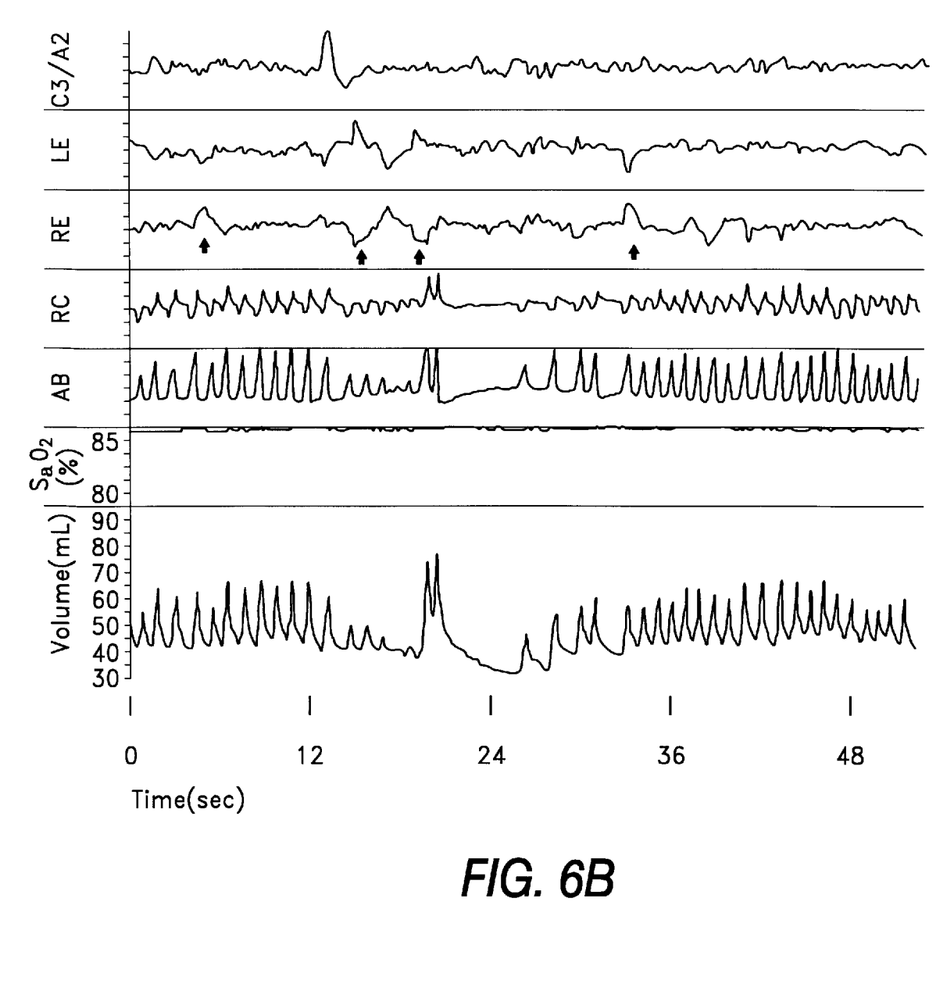

Polysomnographs (PSG) of infants studied in the VDP are presented in FIGS. 6($a$) and ($b$) illustrating the ability to record tidal volume, FRC changes and sigh volume in unsedated sleep.

FIG. 6($a$) is a sample recording of a 2.2 kg infant of corrected age 36 weeks studied in the plethysmograph. An exaggerated form of expiratory braking is illustrated, the RIP is suggestive of respiratory paradox. The vertical line shows lag in the RC expiration signal relative to actual volume loss.

FIG. 6($b$) is a recording of an infant with bronchopulmonary dysplasia at 41.5 weeks corrected age and weight 3.8 kg. REM sleep shows fluctuations in the baseline of the spirometer signal. This represents FRC variations in the order of 20 mls over the epoch displayed.

Note: All records show from the top down, EEG (C3/A2) EOG leads (LE, RE), rib cage (RC) and abdominal (AB) RIP signal, oxygen saturation (SaO$_2$) and volume displacement signal. Inspiration is up on both RIP and volume signals. Arrows denote eye movement.

FIG. 6($a$) illustrates how misleading conventional RIP can be in accurately representing tidal breathing. The RIP channels appear on first inspection to be typical paradox. However, analysis of the volume channel shows that this infant is adopting an exaggerated form of expiratory braking or breath hold. It can be seen that the paradoxical inward chest wall movement is in fact partly due to expiration of the previous breath.

The continuation of RC contraction beyond end expiration reflects the response of the compliant chest wall to the commencement of the next inspiratory effort.

The described plethysmograph is suitable for monitoring tidal volume, respiratory rate and changes in PRC in unsedated sleep in infants with and without lung disease. It enables data to be obtained in REM and NREM sleep. The mechanical properties of the plethysmograph and spirometer are suitable for recording tidal breathing parameters in infants. The spirometer could also be developed and used in more traditional apparatus displaying adequate frequency response, resolution and linear dynamic range for monitoring tidal breathing in infants. The differentiated volume signal (flow) would be suitable for the determination of tidal breathing timing indices such as time to peak expiratory flow/expiratory time ($T_{PEF}/T_E$). The advantages of the spirometer over a pneumotachograph are stability of calibration, reduced resistive load and low frequency response extending to OHz. (The inferior low frequency response of the pneumotachograph is due to very small pressure drops across the resistive element at low flows which make it less likely to accurately resolve slow FRC drifts seen in sleep).

The neck seal 20 is comfortable, easy to apply and permits natural sleep as well as being mechanically stable. Mechanical stability ensures volume displacements within the box are accurately represented by the spirometer without deformation of the neck seal. Minimal contact pressure is required on the neck of the infant in order to obtain a seal because of the very small static pressure of the spirometer.

The plethysmograph of this invention allows monitoring of FRC change on a breath to breath basis over protracted periods of time thus allowing a quantitative measure of FRC instability to be made in infants. (In order to show changes in FRC over relatively long periods the DC coupled mode should preferably be used). This data is otherwise unobtainable with the washout/dilution techniques and with constant volume plethysmography which tenders a static measurement of FRC. These known techniques also require the use of a face mask and pneumotachograph. The use of face mask and pneumotachograph may alter FRC by the effects of resistive loading on timing indices, trigeminal stimulation and increased dead space.

The plethysmograph of this invention permits dynamic measuring of tidal volume and change in FRC without the use of a face mask. The device is suitable for monitoring sleeping infants for prolonged periods without sedation. The device is simply and quickly calibrated. Furthermore, the interpretation of respiratory phenomena derived from conventional non invasive monitoring is enhanced. The plethysmograph could also be used to investigate other dynamic respiratory mechanics of the sleeping infant. The "head out" construction also permits various therapeutic interventions to be monitored without orofacial stimulation.

The foregoing describes only one embodiment of the invention, and modifications which are obvious to those skilled in the art may be made thereto without departing from the scope of the invention.

Although the spirometer and neck seal have been described with particular reference to their use in the plethysmograph, they are able to be used independently in other applications. For example, the spirometer may be used to measure small volume changes with high sensitivity in both physiological (e.g. lung compliance, limb occlusion) and non-physiological applications. Similarly, the neck seal can be used in physiological (e.g. limb splinting) and non-physiological applications.

I claim:

1. Apparatus adapted for monitoring changes in volume of a portion of a body, comprising:
    a first chamber adapted to receive the body portion in use, so that the body portion is located within the first chamber but the remainder of the body is outside the first chamber during use, the first chamber being substantially dimensionally constant in use;
    a movable cover member at least partially defining a second chamber of variable volume;
    an opening in the first chamber providing fluid communication between the first and second chambers; and
    movement detection means for detecting movement of the cover member in response to variation in volume of the second chamber resulting from
    changes in volume of the body portion, the first and second chambers being sufficiently closed during use such that changes in the volume of the body can be detected by the movement detection means.

2. Apparatus as claimed in claim 1, wherein the apparatus is a plethysmograph adapted for monitoring pulmonary function of an infant, such that when in use, a portion of the infant's body below the neck can be located within the first chamber and a head of the infant is located outside the first chamber.

3. Apparatus as claimed in claim 2, wherein the first chamber has a neck seal adapted to provide an airtight seal around the infant's neck in use.

4. Apparatus as claimed in claim 3, wherein the neck seal comprises:
    a pair of juxtaposed flexible sheets each having an opening therein, the openings being aligned, the sheets being sealed together around the openings and along a closed figure extending around, and spaced from, the openings, to define a closed space between the sheets;
    a particulate material in the closed space; and
    a port in at least one of the sheets to permit the closed space to be evacuated,
    whereby upon evacuation of air from the closed space, the seal adopts a substantially rigid form sufficient to maintain a constant volume in the first chamber during use.

5. Apparatus as claimed in claim 4, wherein the flexible sheets are made of elastomeric material.

6. Apparatus as claimed in claim 1, wherein the first chamber is a box, of which at least one side is transparent.

7. Apparatus as claimed in claim 1, further comprising a spigot communicating with the opening, the spigot being located above the body portion and extending upwardly from an upper side of the first chamber, the apparatus further comprising a formation surrounding the spigot and adapted to hold a liquid in use, the movable cover member being a bell extending into the liquid, wherein the second chamber of variable volume is defined by the bell, the surface of the liquid, and the spigot.

8. Apparatus as claimed in claim 1, wherein the movable cover member is a bell connected to at least one radial arm extending from a shaft rotatable about a longitudinal axis thereof, such that movement of the bell results in rotation of the shaft.

9. Apparatus as claimed in claim 8, wherein the movement detection means comprises means for detecting the angular position of the shaft.

10. Apparatus as claimed in claim 8, wherein the bell has a first pair of opposed parallel side walls, and a second pair of opposed curved walls which are concentric with the longitudinal axis of the shaft.

11. A method of using the apparatus of claim 3 to monitor pulmonary function of an infant, the method comprising placing the neck seal around the neck of the infant and locating the infant in the first chamber but such that the head of the infant is outside the first chamber; and using the movement detection means to measure volume changes in the second chamber caused by infant respiratory function within the first chamber.

12. A method as claimed in claim 11, further comprising displaying the volume changes over a period of time so as to show function residual capacity of the infant.

13. A method of monitoring volume changes of a portion of a body, comprising:

enclosing a body portion in a first chamber with a substantially constant volume while maintaining a remainder of the body outside the first chamber, the first chamber having an opening in fluid communication with a second chamber defined in part by a movable cover member, wherein the first and second chambers are sealed from an outside, and the second chamber has a variable volume; and measuring volume changes of the body portion in the first chamber by detecting movement of the cover member in response to variation of the volume of the second chamber caused by the flow of fluid between the first and second chambers.

14. The method as defined in claim 13, further comprising displaying the volume changes over a period of time.

15. The method as defined in claim 13, wherein the enclosing step further comprises providing an airtight seal around a border dividing the body portion within the first chamber and the remainder of the body outside the first chamber.

16. The method as defined in claim 15, wherein the providing the airtight seal around the border comprises:

surrounding the border with a seal member so as to enable placement of the body portion within the first chamber and the remainder outside the first chamber, the seal member having a pair of juxtaposed flexible sheets, each having an opening therein, the openings being aligned, the sheets being sealed together around the openings and along a closed figure extending around, and spaced from, the openings, to define a closed space between the sheets, the closed space being filled with a particulate material, and evacuating air from the closed space from a port in at least one of the sheets, whereby the seal member adopts a substantially rigid form so that the first chamber has the substantially constant volume.

17. The method as defined in claim 13, wherein the enclosing step is adapted to enclose a portion of an infant's body below the neck within the first chamber and to locate a head of the infant outside the first chamber, and the airtight seal is adapted to be placed around the infant's neck.

* * * * *